United States Patent
Vogt et al.

(10) Patent No.: US 10,342,588 B2
(45) Date of Patent: Jul. 9, 2019

(54) PASTE APPLICATION DEVICE FOR MIXING A PASTE

(71) Applicant: Heraeus Medical GmbH, Wehrheim (DE)

(72) Inventors: Sebastian Vogt, Erfurt (DE); Thomas Kluge, Vallendar (DE)

(73) Assignee: HERAUES MEDICAL GMBH, Wehreim (DE)

( * ) Notice: Subject to any disclaimer, the term of this patent is extended or adjusted under 35 U.S.C. 154(b) by 363 days.

(21) Appl. No.: 15/287,789

(22) Filed: Oct. 7, 2016

(65) Prior Publication Data

US 2017/0128113 A1    May 11, 2017

(30) Foreign Application Priority Data

Oct. 9, 2015    (DE) .................. 10 2015 117 270

(51) Int. Cl.
- *A61B 17/88* (2006.01)
- *B05C 17/005* (2006.01)
(Continued)

(52) U.S. Cl.
CPC ...... *A61B 17/8822* (2013.01); *A61B 17/8819* (2013.01); *A61B 17/8833* (2013.01);
(Continued)

(58) Field of Classification Search
CPC .................. A61B 17/8822; A61B 17/8833
See application file for complete search history.

(56) References Cited

U.S. PATENT DOCUMENTS

| 2,446,501 A | 8/1948 | Weber |
| 2,818,999 A | 1/1958 | Miller |
(Continued)

FOREIGN PATENT DOCUMENTS

| CN | 105816234 A | 8/2016 |
| DE | 2036423 A1 | 3/1971 |
(Continued)

OTHER PUBLICATIONS

Kuehn, Klaus-Dieter; "Knochenzemente fuer die Endoprothetik"; Springer-Verlag, 2000, pp. 18-19, Springer-Verlag of BertelmannSpringer publishing group, Berlin, Germany.
(Continued)

*Primary Examiner* — Andrew Yang
(74) *Attorney, Agent, or Firm* — Norris McLaughlin, P.A.

(57) ABSTRACT

A paste application device stores two starting components for mixing the starting components to form a paste and for application of the formed paste. The device comprises a two-component cartridge comprising two internal spaces, two feed plungers shiftable in the internal spaces and bordering the internal spaces on a first side of the two-component cartridge, and at least two dispensing openings by means of which the internal spaces are open on a second side of the two-component cartridge that is opposite from the first side. The device further comprises a hollow cylinder that is made of a plastic material and has one front face that is open and one front face that is partially closed, in which is situated an axially mobile plunger that has at least two pestles attached to it, wherein the at least two pestles are oriented in the direction of the open front face, wherein the open front face of the hollow cylinder is arranged to axially touch against the first side of the two-component cartridge, and a connector for a compressed gas cartridge extends through an opening in the pressure vessel wherein a flap
(Continued)

Figure 1:
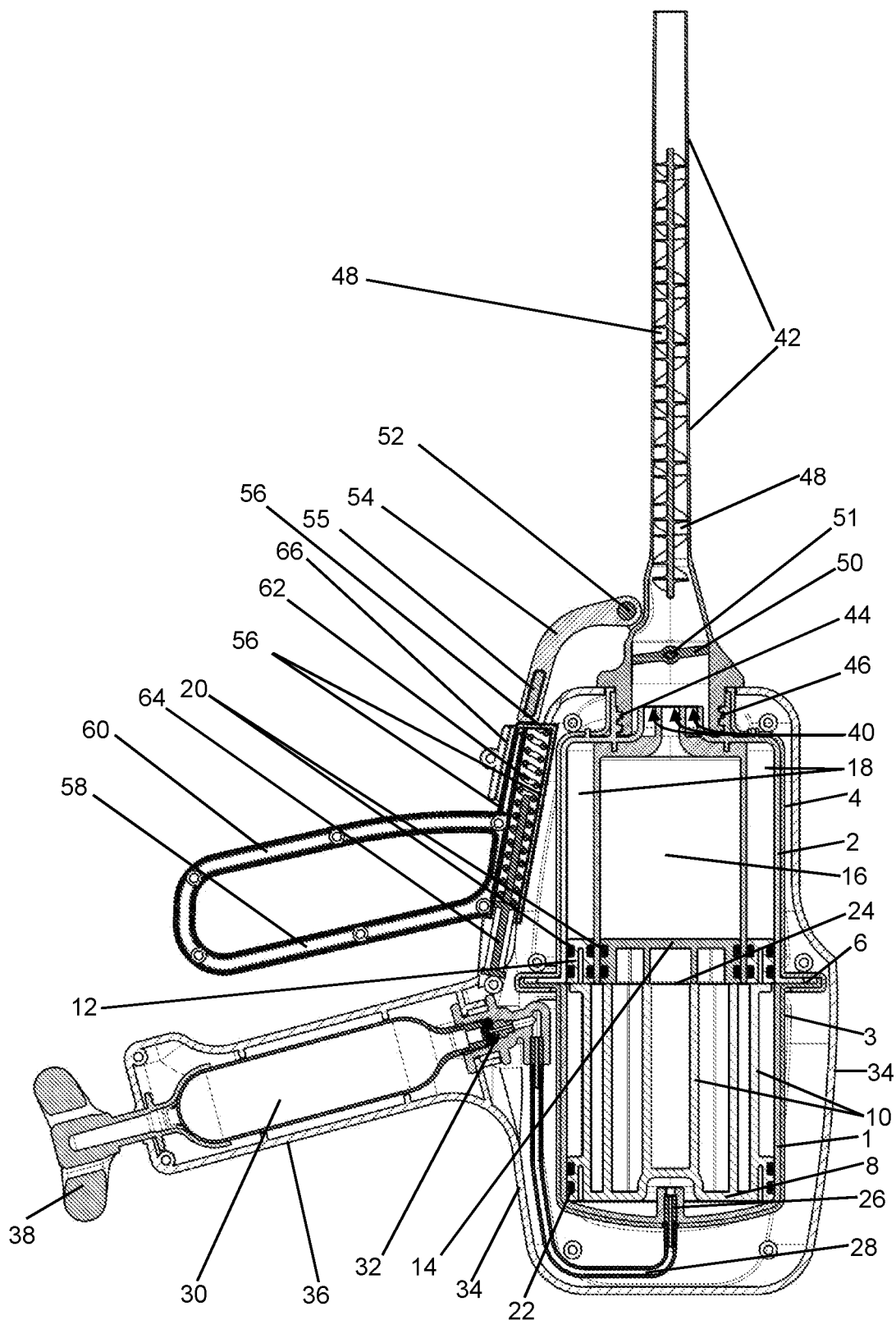

valve can be used to regulate the volume flow of the starting components through the dispensing openings, and whereby the flap valve is operable by means of a rod assembly of the paste application device, whereby the rod assembly is supported with a clearance of at least 0.3 mm in at least one direction that is perpendicular to the main direction.

25 Claims, 7 Drawing Sheets

(51) Int. Cl.
*B05C 17/015* (2006.01)
*B05C 17/01* (2006.01)

(52) U.S. Cl.
CPC .. *B05C 17/00503* (2013.01); *B05C 17/00559* (2013.01); *B05C 17/00573* (2013.01); *B05C 17/015* (2013.01); *A61B 2017/8838* (2013.01); *B05C 17/00576* (2013.01); *B05C 17/0146* (2013.01)

(56) References Cited

U.S. PATENT DOCUMENTS

| | | | |
|---|---|---|---|
| 3,587,930 A | | 6/1971 | Schultz et al. |
| 4,386,717 A | * | 6/1983 | Koob ............... B05C 17/00553 222/94 |
| 4,925,061 A | | 5/1990 | Jeromson et al. |
| 5,893,486 A | | 4/1999 | Wasmire |
| 6,425,897 B2 | * | 7/2002 | Overes ............... A61B 17/8822 606/92 |
| 6,935,541 B1 | | 8/2005 | Campbell et al. |
| 9,901,953 B2 | | 2/2018 | Vogt |
| 2004/0074927 A1 | | 4/2004 | Lafond |
| 2008/0086079 A1 | | 4/2008 | Williamson et al. |
| 2008/0208114 A1 | | 8/2008 | Landau et al. |
| 2009/0105144 A1 | | 4/2009 | Vogt et al. |
| 2009/0105366 A1 | | 4/2009 | Vogt et al. |
| 2011/0272433 A1 | | 11/2011 | Vogt et al. |
| 2016/0082454 A1 | | 3/2016 | Vogt et al. |
| 2016/0214135 A1 | | 7/2016 | Vogt |

FOREIGN PATENT DOCUMENTS

| | | |
|---|---|---|
| DE | 3518780 A1 | 11/1986 |
| DE | 87 16 355 U1 | 2/1988 |
| DE | 202005010206 U1 | 9/2005 |
| DE | 102007052116 A1 | 4/2009 |
| DE | 102007050762 B3 | 5/2009 |
| DE | 102008030312 A1 | 1/2010 |
| DE | 102010019223 A1 | 11/2011 |
| DE | 10 2014 113816 B3 | 7/2015 |
| EP | 1118313 A1 | 7/2001 |
| EP | 3 050 634 A1 | 8/2016 |
| SU | 1 271 581 A1 | 11/1986 |

OTHER PUBLICATIONS

European Search Report for corresponding European Application No. 16187677.6, dated Feb. 22, 2017.

Office Action corresponds to Chinese Application No. 201610879024.8 dated Mar. 1, 2019.

* cited by examiner

PASTE APPLICATION DEVICE FOR MIXING A PASTE

This application claims foreign priority benefit under 35 U.S.C. 119 of German Application No. DE 10 2015 117 270.4 filed Oct. 9, 2015.

The invention relates to a paste application device for storage of two starting components, for mixing the starting components to form a paste, and for application of the paste.

The invention further relates to a method for mixing and dispensing a paste.

Accordingly, the object of the invention is a manually operable paste application device designed for dispensing pasty masses, in particular pasty polymethylmethacrylate cement dough (PMMA cement dough). The paste application device and the method are further intended for storing, mixing, and dispensing pasty two-component systems. The device is intended for single use only.

Conventional polymethylmethacrylate bone cements (PMMA bone cements) are usually made from a powdered component and a liquid monomer component (K.-D. Kühn: Knochenzemente für die Endoprothetik: ein aktueller Vergleich der physikalischen and chemischen Eigenschaften handelsüblicher PMMA-Zemente. Springer-Verlag Berlin Heidelberg N.Y., 2001). After mixing the cement powder with the liquid monomer component, said PMMA bone cements are applied in their non-cured pasty state in the form of cement dough. If mixing systems are used with powder-liquid cements, the cement dough is situated in a cartridge. The cement dough is squeezed from said cartridge through the motion of a feed plunger. Said motion of the feed plunger can be effected by means of a mechanical application device.

In the case of pasty two-component pastes and/or two component bone cements, such as are known, for example, from DE 10 2007 050 762 B3, DE 10 2008 030 312 A1 or DE 10 2007 052 116 B4, both pasty components are stored in two separate cartridges with two separate feed plungers. During application, both pastes are pressed from the interior spaces of the cartridge into a static mixer through the motion of the feed plungers and are dispensed through a dispensing tube once the mixing is completed.

The application of pasty adhesives and sealants is done basically the same way using paste application devices.

Currently, paste application devices that can be driven manually or pneumatically or electrically are used to extrude thick viscous masses. Customary simple mechanical paste application devices utilise, in particular, clamp rods that are driven by a manually-operated tilting lever for extrusion. In the case of highly viscous pastes, said devices can be operated only by exerting very strong forces. This exertion of force is unreasonable for medical users in the OR.

Electrically-driven extrusion devices can be driven both with rechargeable batteries and/or batteries or by means of a stationary electrical power supply. Said devices can extrude particularly thick pasty masses since their force is very large in some cases. However, it is one disadvantage of the use of electrical motors that these motors contain non-ferrous metals and are expensive. Moreover, rechargeable batteries must be kept in stock or a cable connection, which is an impediment in the OR area, must be provided by means of which the paste application device must be connected to a power network.

Pneumatic paste application systems, like the systems known, for example, from U.S. Pat. No. 2,446,501 A, DE 20 2005 010 206 U1, US 2004 074 927 A1 or U.S. Pat. No. 6,935,541 B1, require a compressed air connection. This necessitates compressed air hoses, which may impede the mobility of the user and the use of the paste application system. Alternatively, the use of compressed gas cartridges to provide compressed gas is feasible just as well. Documents U.S. Pat. No. 2,818,999 A and EP 1 118 313 A1 shall be cited as being exemplary in this context. In this context, devices have been proposed (in printed specifications US 2004 074 927 A1 and U.S. Pat. No. 6,935,541 B1 cited above), in which the compressed gas influx is controlled by a valve and, in addition, the flow of the viscous mass is controlled by a second valve. In these devices, the gas cartridges are integrated into the devices. These devices are disadvantageous in that two valves are being used.

An interesting proposal is described in EP 4 925 061 A1. This system has no gas cartridge arranged in the device. The device needs to be filled with compressed gas by means of a valve prior to its application. Said device contains a cartridge, in which the viscous mass is arranged. A plunger that is connected to one end of the cartridge by means of a bellows is arranged behind the viscous mass. Before application, a liquid gas is filled through a valve into the hollow space formed by the plunger, the bellows, and the cartridge end. This proposal has to be seen in a critical light, since the expansion of liquid gas is associated with cooling which may lead to the elastic bellows becoming brittle. If the bellows becomes brittle, leakiness cannot be excluded. As a result, compressed gas can exit through the bellows and penetrate into the viscous mass adjacent to the plunger. Any mixing of the pastes with compressed gas is unacceptable in the case of polymethylmethacrylate bone cement pastes. Gas bubbles would weaken the cured polymethylmethacrylate bone cement. Moreover, the liquid compressed gas is difficult to fill into the receptacle and it is unreasonable to expect users in the OR to do this.

Patent DE 10 2010 019 223 B4 proposes a cementing device, in which a compressed gas cartridge is punctured by means of the motion of a rotary valve. The compressed gas presses directly onto the plunger of the device. The dispensation of the pastes is regulated by a valve. It is a disadvantage of said device that high-strength plastic materials need to be used for the cartridges, since no pressure vessel is provided.

Basically, it is feasible with all compressed gas-driven paste application devices having feed plungers that the compressed gas passes by the feed plunger into the pastes in unwanted manner. This issue may be more pronounced the higher the gas pressure is.

Moreover, devices for the dispensation of medications are known from the field of medicine that also utilise compressed gas cartridges as energy source, although no regulation of the volume flow of the medication by means of valves is provided (US 2008 086 079 A1, US 2008 208 114 A1). Systems of this type are not very useful for bone cements, since they do not allow for specific portioning of the bone cement dough during the operation.

It is the object of the invention to overcome the disadvantages of the prior art. Specifically, a paste application device and a method for mixing and dispensing of a paste are to be found by means of which even very viscous starting components can be stored, mixed, and dispensed using a simple design. The paste application device should be easy to operate by hand, whereby, preferably, only one hand is needed to hold and operate the paste application device. In this context, the paste application system shall be sufficiently inexpensive to enable its single use (disposable article).

Disposable articles are particularly advantageous in surgical theatres due to the existing strict hygienic requirements. The paste application device should also be compact in design to render it easy to handle.

It is also the object of the invention to overcome the disadvantages of the previously known paste application devices for storing, mixing and applying pasty polymethylmethacrylate bone cements, in which the energy for the mixing and the application is provided by a compressed gas cartridge that is integrated into the device. It shall be feasible to hold the device with just one hand, whereby the dispensation of the mixed cement dough shall be controlled with the same hand that holds the device. Normal manual force shall be sufficient for actuation. In this context, it shall be feasible to reliably start (and/or this continue) and stop the dispensation of the bone cement.

Moreover, one object of the invention is to provide a paste application device that can be driven without the use of external stationary energy sources, such as compressed air or electrical current, and that is capable of extruding and mixing viscous pasty masses. In addition, the paste application device shall contain no copper and no copper alloys. Moreover, it shall be feasible for the user to use it independent of location and it shall have a maximally simplified structure. A device that is suitable for storing, mixing, and dispensing highly viscous pasty polymethylmethacrylate bone cement is to be developed, whereby compressed gas that is stored in a compressed gas cartridge that is integrated into the device is to be used as the energy source. Moreover, it shall be feasible to provide an inexpensive paste application device that is intended for single use only. Moreover, it is another object of the invention to develop a method for the dispensing of pasty masses by means of the paste application device to be developed.

Moreover, it shall be feasible to store two cement pastes separately in the paste application device before applying the cement. Moreover, it must be feasible to sterilise the surface of the paste application device with ethylene oxide. It is important that the high-pressure required during the application does not lead to undesired leakage of cement, which might lead to contamination of the medical user and surgical theatre (OR room). It should be possible to manually operate the paste application device with as little force as possible. Another important point for application is that no substantial amounts of the cement dough and/or paste continue to flow out when the operation of the paste application device is stopped.

Moreover, a device that is suitable for storing, mixing, and dispensing highly viscous pasty polymethylmethacrylate bone cement is to be developed, whereby compressed gas that is stored in a compressed gas cartridge that is integrated into the paste application device is to be used as the energy source. It is another object of the invention to provide for the paste application device to safely tolerate, mechanically, high gas pressures in excess of 30 bar over an application period of a few minutes without the paste application device becoming deformed or destroyed. Moreover, the production of the paste application device to be developed shall be inexpensive. Moreover, the paste application device should contain no compressed gas flow-regulating valves and no separate devices intended for evaporation of liquid compressed gas. The paste application device to be developed shall be designed sufficiently robust such that the compressed gas can be present as a mixture that also contains liquefied compressed gas. If liquid carbon dioxide is used as compressed gas, the paste application device must also tolerate mixtures of gaseous, liquid, and solid carbon dioxide without mechanical damage or deformation.

The objects of the invention are solved by a paste application device for storage of two starting components, for mixing the starting components to form a paste, and for application of the paste, comprising a two-component cartridge comprising two internal spaces, two feed plungers that can be shifted in the internal spaces and border the internal spaces on a first side of the two-component cartridge, and at least two dispensing openings by means of which the internal spaces are open on a second side of the two-component cartridge that is opposite from the first side, a hollow cylinder that is made of a plastic material and has one front face that is open and one front face that is partially closed, in which is situated an axially mobile plunger that has at least two pestles attached to it, whereby the at least two pestles are oriented in the direction of the open front face, whereby the open front face of the hollow cylinder is arranged to axially touch against the first side of the two-component cartridge, and whereby the plunger closes in gas-tight manner against the internal walls of the hollow cylinder, whereby the two-component cartridge and the hollow cylinder are arranged in a pressure vessel, whereby the hollow cylinder comprises, on the front face that is partially closed, a connector for a compressed gas cartridge that extends through an opening in the pressure vessel, whereby a manually operable flap valve is arranged downstream from the dispensing openings or a dispensing tube having a manually operable flap valve can be attached downstream from the dispensing openings, whereby the flap valve thus arranged can be used to regulate the volume flow of the starting components through the dispensing openings.

The flap valve can be operable by means of a rod assembly of the paste application device, whereby the rod assembly is supported such as to be mobile in one main direction with respect to the hollow cylinder and is supported with a clearance of at least 0.3 mm in at least one direction that is perpendicular to the main direction.

Being able to regulate the volume flow of the starting components through the dispensing openings means, in particular, that the volume flow can be stopped by closing the flap valve.

The internal spaces of the two-component cartridge are preferably cylindrical in shape and the feed plungers are arranged such as to be axially shiftable in the internal spaces.

According to the invention, a cylinder geometry shall be understood to be the general cylinder shape with any footprint and therefore not only cylinders with a circular footprint.

Preferably, the rod assembly is guided in a guidance such as to be mobile in the main direction.

The invention can preferably provide the manually operable flap valve to be operable by means of a trigger on a handle of the paste application device.

According to the invention, the paste application device can preferably be held by one hand and the flap valve can be operated by the same hand. As a result, the use of the paste application device is made simpler.

The internal spaces are preferably filled with two starting components, which are to be mixed and of which at least one is a paste, whereby the mixed starting components particularly preferably form a PMMA bone cement. It shall be feasible to apply the mixture with the paste application device.

Preferably, the plunger closes against the internal walls of the hollow cylinder not only in gas-tight manner, but even in pressure-tight manner up to at least 10 atmospheres and/or up to at least 1,000 kPa, particularly preferably in pressure-tight manner up to at least 3,000 kPa.

Preferably, the rod assembly is supported with a clearance of at least 1 mm in at least one direction that is perpendicular to the main direction, particularly preferably with a clearance of at least 2 mm.

Moreover, the flap valve is preferably arranged outside of the pressure vessel. According to the invention, the axle of the flap valve preferably consists of steel in order to be able to receive the forces acting on the flap without deformation or destruction.

According to a particularly preferred refinement of the present patent application, the paste application device comprises a manually operable trigger by means of which the rod assembly can be moved in the main direction and by means of which the flap valve can thus be operated.

As a result, the paste application device is easy to operate. Specifically if a handle of the kind of a pistol handle is provided on the underside of the paste application device and a trigger is situated within reach of the fingers of one hand of the user, the paste application device is comfortable to operate with one hand such that the other hand remains unoccupied and/or available for other activities during the surgery.

In this context, the invention can provide the trigger to comprise two levers situated at a distance from each other between which at least one finger of a hand can reach such that the trigger can be moved in both directions with the at least one finger of the hand, whereby the first lever is operated by pulling the trigger and thus opens the flap valve, and the second lever is operated by pushing the trigger in reverse direction and thus closes the flap valve.

The distance between the two levers of the trigger is at least 1.5 cm, preferably at least 3 cm, to allow the at least one finger of the hand of a user to reach between the levers.

As a result, the trigger can be used not only to open the flap valve, but also to manually close the flap valve by pushing the trigger in reverse direction by means of the second lever using the same hand.

Moreover, the invention can provide the trigger to transition the flap valve from the closed to the maximally opened state by means of a stroke of maximally 100 mm, preferably by means of a stroke between 2 mm and 40 mm, particularly preferably by means of a stroke between 5 mm and 15 mm.

The maximally opened state of the flap valve is the state, in which the flap valve has been opened maximally by means of the paste application device. Possibly, the flap valve can be opened even further outside the paste application device, but this is not feasible by means of the paste application device.

Said stroke can still be generated through a motion of the fingers of a hand such that the paste application device is easy to operate.

According to a further preferred refinement, the present invention can provide at least one restoring element to appropriately act on the rod assembly and/or flap valve such that the restoring element rotates the flap valve into the closed position, whereby, in particular, the restoring element is a compression spring that is supported on a part of a housing that is connected to the hollow cylinder, whereby, preferably, the at least one restoring element can be tensioned by pulling the trigger.

As a result, the restoring element rotates the flap valve of the paste application device in the direction of the closed position, when the user no longer pulls the trigger and/or the first lever into the position for opening the flap valve.

Having the second lever of the trigger is of great advantage in this context as well, since lightly tapping on the second lever with the back of a finger can be used to overcome an initial resistance, such as, for example, adhesive friction, and additional pressure for closing the flap valve, i.e. for overcoming the final resistance via the second lever and the rod assembly, can be exerted on the flap valve.

In this context, the invention can provide the restoring element to be a compression spring that is supported on a part of a housing that is connected to the hollow cylinder.

This embodiment is particularly easy and inexpensive to implement.

Moreover, the invention can provide the pressure vessel to touch against the hollow cylinder or to be situated at a distance of at most 0.4 mm from the hollow cylinder, preferably of at most 0.1 mm, particularly preferably of at most 100 μm, and yet more preferably of at most 50 μm.

The pressure vessel can receive the pressure forces even if there is a small distance of at most 0.4 mm between the pressure vessel and the hollow cylinder, since the relaxation of the gas from the compressed gas cartridge proceeding when the compressed gas is conducted from the compressed gas cartridge into the hollow cylinder is associated with an expansion (partial adiabatic expansion), during which the relaxing gas cools down, which in turn cools the surrounding containers and, as a result, the hollow cylinder made of plastic material contracts less strongly than the pressure vessel, if the latter is made of metal or metal alloy, and, as a result, the metallic pressure vessel touches against the hollow cylinder. A small distance of maximally is 0.1 mm or less is preferred though, in order to enable low deformation and firmer seating of the pressure vessel. At distances of 100 μm at most, the pressure vessel of the paste application device can receive the pressure without major deformation of the hollow cylinder and of the two-component cartridge. The external wall of the two-component cartridge preferably consists of plastic material. The feed plungers can also be made from plastic material, whereby it is preferred, in addition, to arrange on the feed plungers circumferential gaskets for sealing the feed plungers with respect to the internal spaces. Moreover, wiper lips can be arranged on the feed plungers by means of which the content of the internal spaces can be expelled from the internal spaces either completely or at least 99% thereof.

To attain a more compact design of the paste application device, the invention can provide a compressed gas conduit to be connected to the connector for the compressed gas cartridge, whereby the compressed gas conduit connects the connector to the compressed gas cartridge or to an opening device for the compressed gas cartridge, whereby, preferably, the compressed gas conduit is a fabric-reinforced plastic hose.

As a result, the compressed gas cartridge can be accommodated on the underside or in the handle of the paste application device such that the device does not become too bulky and unwieldy, which would adversely affect the usability.

Preferred paste application devices can also be characterised in that the pressure vessel is made from metal, a metallic alloy, a high-strength plastic material, a fibre-reinforced plastic material or a combination thereof, whereby the pressure vessel preferably consists of a metal or a metallic alloy.

In this context, the invention preferably provides the pressure vessel to consist of aluminium, zinc, an aluminium alloy or steel.

Metals or metal alloys are preferred as material for the pressure vessel, since many metallic materials are easy to process despite their high compressive strength and/or despite their high tensile strength. Conceivable high-strength plastic materials for the pressure vessel include duroplasts, polyamides, polyamide-co-imides, polysulfones, polyketones, and polyetherketones, although these are more difficult to process than metals or metal alloys and are therefore less preferred as material for the pressure vessel. Glass fibre-reinforced plastic materials are particularly preferred as fibre-reinforced plastics.

Moreover, the invention can provide a yoke or an arch to be attached on the rotary axis of the flap valve in force-locking or form-fitting manner and the yoke or arch to be connected to the rod assembly by means of an axle.

As a result, good transmission of force to the rotary axis of the flap valve is attained such that the paste application device can be operated reliably.

In this context, the invention can provide the axle, by means of which the yoke or the arch is connected to the rod assembly, to be arranged such as to be parallel to the rotary axis of the flap valve, whereby said axle is preferred to be arranged on the apex of the arch or yoke.

This attains a symmetrical transmission of force and optimal use of the lever that is formed by the yoke or arch. Moreover, inhomogeneous mechanical stresses acting on the paste application device in the area of the flap valve are thus prevented.

According to an advantageous refinement, the present invention can just as well provide the rod assembly to have a two-part design, whereby the two parts of the rod assembly are or can be connected to each other by means of a fastening means, in particular a bolt, slider or a snap-in element, preferably are or can be connected to each other in a form-fitting manner, whereby a first part of the rod assembly is preferably connected to the dispensing tube and a second part of the rod assembly is connected to the hollow cylinder.

As a result, the flap valve can be arranged in a separate part, in particular in a dispensing tube, that can be attached to the remaining paste application device only briefly before the use of the paste application device. This allows a closure to be provided that can be replaced by the dispensing tube before application, whereby the closure seals the dispensing openings such that the paste application device is suitable for long-term storage of the starting components as well.

The invention also proposes to arrange a handle on the paste application device by means of which the paste application device can be held with one hand, whereby the rod assembly can be operated with the same hand, in particular by means of the trigger, and thus the flap valve can be opened and closed with the same hand.

As a result, the paste application device is easy to operate.

In this context, the invention can provide the trigger, with the flap valve in its closed state, to be situated at a distance of maximally 30 mm from the handle and the trigger, with the flap valve in its maximally opened state, to touch against the handle or to be situated at a distance of no more than 10 mm from it.

This necessitates that the flap valve can also be operated by means of the trigger.

This is advantageous in that the paste application device can be held and operated easily with one hand.

Moreover, the invention can provide for the compressed gas cartridge or the compressed gas cartridge and an opening device for opening the compressed gas cartridge to be arranged in the handle.

This allows the external dimensions of the paste application device to be kept small. Moreover, the compressed gas cartridge can be opened inside the paste application device.

Paste application devices according to the invention can also be provided such that the flap valve is arranged in a conduit that is formed by a dispensing tube, whereby it is preferred to have, in addition, a static mixer provided in the dispensing tube by means of which the starting components can be mixed by the static mixer while they flow through the dispensing tube.

This allows for a particularly simple design to be attained that can be implemented inexpensively and at the same time is insensitive to failure and is sufficiently stable for the regulation of high-pressure flows of the starting components.

Moreover, the invention can provide the pressure vessel to have a two-part design, whereby the two parts are connected to each other in force-locking manner by riveting, by a screw connection and/or by a union nut, whereby a first part of the two parts of the pressure vessel preferably contains the two-component cartridge and the second part of the two parts of the pressure vessel contains the hollow cylinder.

This simplifies the production and assembly of the paste application device. In particular, filling the two-component cartridge with the starting components is simplified clearly by this means. Preferably, the two parts of the pressure vessel are connected to each other in form-fitting and/or material-bonded manner, particularly preferably are connected to each other by means of a folded seam.

Preferred embodiments of the invention can be characterised in that the two-component cartridge, or at least regions thereof, is a coaxial cartridge, whereby one of the internal spaces in the coaxial cartridge is cylindrical and situated inside and the other internal space is cylindrical and coaxially surrounds the inner internal space.

The feed plungers are adapted to match the internal shape of the cylindrical internal spaces. The cylinder shape is advantageous because the strong forces occurring during the extrusion of the starting components and/or during the application of the pressure from the compressed gas cartridge to the two-component cartridge can be received uniformly by the pressure vessel. Moreover, it is feasible to manufacture components with cylindrical geometry inexpensively.

To enable storage of the starting components of the bone cement, the invention can provide the paste application device to comprise a closure for closing the dispensing openings that can be fastened by means of a fastening means of the closure, in particular by means of a thread of the closure, to an opposite fastening means in the region of the dispensing openings, in particular to an opposite thread in the region of the dispensing openings, whereby it is preferred that the dispensing tube, which also comprises a corresponding fastening means for this purpose, can be fastened to the opposite fastening means.

As a result, the starting components can be stored in the paste application device for a longer period of time, since the closure affords a better and more air-tight closure of the internal spaces containing the starting components as compared to only the valve element sealing the internal spaces.

In this context, the invention can provide the closure to be a key for opening the compressed gas cartridge and/or for connecting the compressed gas cartridge to the opening a means for opening the compressed gas cartridge, whereby the closure preferably can be plugged, on the floor-side, onto the compressed gas cartridge as a key thus rendering the compressed gas cartridge movable, in particular rotatable and/or shiftable in longitudinal direction, for opening the compressed gas cartridge and/or for connecting the compressed gas cartridge to the opening means for opening the compressed gas cartridge.

As a result, premature inadvertent opening of the compressed gas cartridge can be prevented such that the operation of the paste application device is simplified.

The invention can just as well provide a compressed gas cartridge fastening means on the connector of the hollow cylinder or on the compressed gas conduit, by means of which the compressed gas cartridge can be attached to the connector and/or to the compressed gas conduit in pressure-tight manner, and/or provide a puncturing mandrel as opening means for opening the compressed gas cartridge on the connector of the hollow cylinder and/or on the compressed gas conduit or provide the opening means to comprise a puncturing mandrel of this type.

This design attains a secure and tight connection and/or prevents premature inadvertent opening of the compressed gas cartridge. The compressed gas cartridge fastening means is preferably an internal thread into which an external thread of the compressed gas cartridge can be screwed. Moreover, a gasket (for example in the form of an O ring) can be provided on a connecting surface and allows better sealing of the connection of the compressed gas cartridge to the hollow cylinder to be attained.

Moreover, in order to improve the storage properties, the invention can provide a protective foil/film to be arranged between the hollow cylinder and the two-component cartridge and the protective foil/film to close the internal spaces of the two-component cartridge on the first side, whereby the protective foil/film preferably is pasted, welded or bonded to the two-component cartridge.

Improved sealing of the internal spaces can be attained by means of the protective foil/film such that longer and/or quality-preserving storage of starting components with volatile ingredients, such as methylmethacrylate, in the internal spaces is made feasible. In operation, the protective foil/film is punctured when the pestles are propelled through the plunger in the hollow cylinder, such that the pestles can propel the feed plungers in the two-component cartridge and thus can extrude the starting components from the two-component cartridge through the dispensing openings from the internal spaces of the two-component cartridge.

The protective foil/film is preferred to be an aluminium composite foil. Aluminium and/or aluminium-coated foils are particularly tight with respect to methylmethacrylate vapours such that the paste application device is then particularly well-suited for storage of the starting components of a PMMA bone cement.

According to the invention, it can be preferred to provide the pressure vessel to have a tensile modulus in accordance with EN ISO 527 in excess of 1,500 MPa.

It can also be preferred according to the invention that the pressure vessel has a compressive strength of at least 3 MPa.

The invention can just as well provide the pressure vessel to comprise a cylindrical internal space for accommodation of the hollow cylinder and the two-component cartridge. The cylindrical geometry is particularly well-suited for receiving the forces and is easy to generate during production.

A refinement proposes to provide in the external wall of the hollow cylinder, namely in the half facing in the direction of the two-component cartridge, and in the wall of the pressure vessel at least one through-going ventilation opening such that the pressure escapes from the hollow cylinder when the plunger is arranged between the ventilation opening and the two-component cartridge.

As a result, the paste application device is rendered free of pressure after extrusion of the starting components and can subsequently be recycled or disposed of without any danger. The ventilation openings connect the space between the two-component cartridge and the axially mobile pestles in the hollow cylinder to the surrounding atmosphere in gas-permeable manner. In this context, the invention can provide the compressed gas to escape into the surroundings when the plunger reaches the end-position in the hollow cylinder.

Preferably, the at least one ventilation opening of the hollow cylinder is arranged in the cylinder jacket wall of the hollow cylinder. Also preferably, the at least one ventilation opening of the pressure vessel is arranged in the cylinder jacket wall of the pressure vessel. It can be particularly preferable to just as well provide the ventilation openings in the hollow cylinder and in the pressure vessel to be arranged such as to overlap with each other. A manually operable valve element for releasing the compressed air can be arranged on the at least one ventilation opening of the pressure vessel.

According to a refinement, the invention can just as well provide the two-component cartridge, the hollow cylinder, and the pressure vessel to be arranged in a housing, whereby it is preferred for the pressure gas cartridge to also be arranged in the housing and/or the housing to be provided on the underside of the paste application device in the form of a handle.

As a result, the paste application device is being closed with respect to the outside. The housing preferably consists of plastic material.

The objects underlying the present invention are also solved through a method for mixing and expelling a paste, characterised by the steps of:

conducting a compressed gas from a compressed gas cartridge through a connector of a hollow cylinder into the hollow cylinder, whereby a pressure vessel receives the force of the compressed gas acting on the walls of the hollow cylinder and a plunger with pestles is propelled in the direction of a two-component cartridge by the compressed gas;

the propelled pestles of the plunger propel the feed plungers into at least two internal spaces of the two-component cartridge, whereby the starting components are expelled from the internal spaces of the two-component cartridge through the at least two dispensing openings of the internal spaces;

whereby the flow of the starting components is stopped by a closed flap valve downstream from the dispensing openings, and a rod assembly is moved by a manual operation of an operating element, and a yoke or an arch is rotated by the motion such that the rotary axis of the flap valve connected to the yoke or arch is rotated such that the flap valve is opened and the starting components and/or the mixture thereof flow(s) through the opened flap valve, and the mixture is applied after mixing the starting components.

In this context, the invention can provide the forces, which occur when the compressed gas is conducted into the hollow cylinder and when the plunger and the feed plunger are propelled in the two-component cartridge, to be taken up by the pressure vessel, in particular by an essentially cylindrical pressure vessel that surrounds the two-component cartridge and the hollow cylinder, whereby the pressure vessel particularly preferably touches against the two-component cartridge and the first hollow cylinder.

Preferably, the invention provides for the use of a paste application device according to the invention for implementation of the method.

Moreover, the invention can provide the flap valve to be closed through the action of a force of a restoring element, in particular of an elastic spring, and/or through a manual operation of the operating element in the direction reverse to the operation for opening the flap valve.

The invention can just as well provide a closure to be removed from the paste application device before conducting the compressed gas into it, and the closure to close the dispensing openings of the internal spaces of the two-component cartridge, and a dispensing tube, in which the flap valve is arranged, to be attached in front of the dispensing openings of the internal spaces. In this context, the invention can preferably provide the compressed gas cartridge to be opened after attachment of the dispensing to and, particularly preferably, the compressed gas to be conducted to the hollow cylinder along with the opening of the compressed gas cartridge.

The invention is based on finding, surprisingly, that, using a pressure vessel and a flap valve that is arranged downstream of the cartridges (downstream of the internal spaces of the two-component cartridge) and is filled with viscous starting components, it is feasible to generate a direct drive of the feed plungers by means of the gas pressure from a compressed gas cartridge without first having to reduce the pressure of the gas. The pressure vessel is capable of receiving the strong attendant forces without the plastic form bodies (the two-component cartridge and the hollow cylinder), which are situated inside, becoming deformed or becoming deformed too strongly. Moreover, despite the presence of the strong attendant forces, the flap valve can be operated by means of a rod assembly by operating the rotary axis of the flap valve by means of a lever on which the rod assembly acts. For this purpose, the bearing of the rod assembly has a clearance of at least 0.3 mm perpendicular to the main direction of motion by means of which the rotary motion of the lever is received. The plastic form bodies, which are situated inside, should be made from plastic material such that the drive elements (the plunger and the feed plungers) can slide well in the plastic form bodies and, at the same time, have a sealing effect. For this purpose, the flap valve must be designed to be sufficiently stable. The positioning in a relatively narrow channel downstream of the internal spaces of the two-component cartridge helps to design the structure of the flap valve sufficiently stable without any major design effort. Theoretically, the flap valve can just as well be arranged downstream of a static mixer, which then further reduces the force acting on the flap valve. As a result, the design can be made to be relatively simple and functional without requiring sophisticated components for conducting and impacting the flow of compressed gas. Reducing the number of components also reduces the sensitivity of the paste application device to malfunction or interference significantly.

The underlying rationale of the invention is to connect the rotary axis of the flap valve to an arch or a yoke in a force-locking or form-fitting manner. A rod is hinged to the apex of the arch or yoke as part of the rod assembly, whereby the rod is arranged on the underside of the housing such as to be parallel to the longitudinal axis of the device. Said rod is mobile such that it can rotate about the longitudinal axis of the arch or yoke. A first lever is arranged at the end of the rod and perpendicular to the rod as part of a trigger. When the first lever is pulled in the direction of the handle by an index finger, middle finger or ring finger, the rod pulls the arch or yoke in the direction of the handle also. In this process, the flap valve is opened by a rotation of the rotary axis. To close the flap valve, the back of the index finger, middle finger and ring finger moves a second lever of the trigger away from the handle. It needs to be noted in this context that only very short distances of a few millimeters each are feasible for deflection of the first lever and second lever for opening and closing the flap valve in order to enable comfortable operation.

Own experiments with compressed gas-driven paste application devices have shown that it is essential that the components exposed to compressed gas are gas-tight and do not strongly deform due to the pressure to the extent that the function of the paste application device would be impaired. In this context, feed plungers of a coaxial cartridge were moved by a drive plunger on which a gas pressure of 30 to 50 bar was made to act. By this means, an extrusion force in the range of 12 to 18 kN was exerted. The volume flow was controlled by an upstream flap valve that could be moved manually by a lever of 11 cm. The flap valve is supported such as to be rotatable by means of a rotary axis. The rotary axis is pushed into the bearing at a force of several kilonewtons. Due to the contact pressure of the rotary axis being this high, the adhesive friction and gliding friction of the rotary axis in the bearing is very high. It was evident in this context that the very high extrusion force necessitates a relatively high torque for control of the flap valve. In particular, the restoration of the flap valve to the closed original state after completed opening can be effected only by very strong restoring springs. This means, if strong restoring springs are used to close the flap valve, the user needs to overcome both the adhesive friction and sliding friction and, in addition, the force of the restoring spring in order to open the flap valve beforehand.

In further experiments, it was found that it is very difficult to store cement cartridges appropriately during the dispensation of the cement pastes, during the propulsion of the feed plungers by pestles, such that the cement cartridges do not move away from the pestles and the pestle drive due to deformation or twisting at internal pressures in excess of 20 bar. Moreover, own experiments have shown that cement cartridges made of aluminium alloys are unsuitable for polymethylmethacrylate cement pastes, since the alloys and the alloy ingredients present in them, such as copper and manganese, effect an undesired radical polymerisation during the storage of cement pastes in the cement cartridge and/or in the internal spaces. Polymethylmethacrylate-containing cement pastes are sufficiently long-term stable on storage only in cement cartridges made from suitable plastic materials, such as poly-acrylonitrile-co-methylmethacrylate and polybutylene terephthalate.

A first, very general exemplary embodiment of the invention shall be described in the following:

An exemplary paste application device is composed of a) a hollow cylinder-shaped first pressure vessel having a minimal compressive strength of 30 bar;

b) at least one plastic cartridge that has an axially mobile dispensing plunger and is arranged in the first pressure vessel c) a dispensing tube that contains a static mixer and a flap valve with a rotary axis and is connected to the plastic cartridge in form-fitting manner, whereby the flap valve is arranged outside of the first pressure vessel;

d) a hollow cylinder-shaped second pressure vessel that has a minimal compressive strength of 30 bar, an open front face, and a closed front face, whereby the closed front face has a perforation, whereby e) the plastic hollow cylinder is arranged appropriately in the second pressure vessel such that a connector into the hollow cylinder projects through the perforation of the second pressure vessel;
f) the gap between the plastic hollow cylinder and the second pressure vessel is smaller than 0.1 mm;
g) an axially mobile plunger (drive plunger) is arranged in the plastic hollow cylinder, whereby the plunger is connected to at least one pestle;
h) an opening device for a gas cartridge is arranged outside of the pressure vessel and is connected to the opening of the hollow cylinder by means of a gas-permeable compressed gas conduit;
i) the two pressure vessels being connected to each other in form-fitting or material-bonded manner; and
j) a closed housing, in which the first pressure vessel, the second pressure vessel, the compressed gas conduit, the opening device of the gas cartridge, and the gas cartridge are arranged.

The invention can just as well provide the paste application device to comprise a plastic hollow cylinder having an open and a closed front face, whereby a hollow cylinder is arranged on the outside of the plastic hollow cylinder and is connected in gas-permeable manner to the internal space of the plastic hollow cylinder and has an external thread on its outside.

Said paste application devices can be characterised in that
a) on the underside of the device the housing is provided in the form of a handle;
b) the two ends of the rotary axis of the flap valve are connected to an arch in form-fitting or force-locking manner;
c) a rod (as rod assembly) is arranged on the apex of the arch and is supported such as to be rotatable about the longitudinal axis of the arch and is oriented parallel to the longitudinal axis of the device;
d) a first lever (as part of the trigger) is arranged at the end of the rod and perpendicular to the rod axis, whereby the first lever, with the flap valve in the closed state, is 5 to 15 mm distant from the front side of the handle;
e) a second lever (as part of the trigger) that is arranged at least 3.0 cm distant from the first lever and perpendicular to the lever axis;
f) a guidance for the rod is arranged on the underside of the housing in front of the handle; and
g) with the flap valve in the opened state, the first lever has a distance of 0 to 5 mm from the handle.

The invention provides the rod to have a two-part design, whereby the two parts of the rod are connected by a slider or a snap-in element in form-fitting manner. The dispensing tube and the flap valve, the arch or the yoke, and the first part of the rod form a sub-assembly. The second part of the rod assembly is held on the housing by the guidance. Once the closure of the cartridge is removed, the sub-assembly is screwed into the cartridge. Then the first part of the rod assembly is connected in form-fitting manner to the second part of the rod assembly by a slider that is attached to the second part or just as well to the first part of the rod assembly. Alternatively, it is feasible just as well for snap-in elements to be arranged on the first part and second part of the rod assembly such that both parts of the rod assembly can be connected to each other through a snap-in mechanism.

It is advantageous to arrange on the rod and/or the rod assembly a spring element that is supported against the handle and pushes the rod assembly in the direction of the arch or yoke. This facilitates the manual restoring motion for closing the flap valve.

The first pressure vessel and the second pressure vessel are made from metal and/or plastic material and/or glass fibre-reinforced plastic materials, whereby the pressure vessels preferably consist of metal. Particularly preferably, the pressure vessels consist of aluminium. Advantageously, the containers can be produced by impact extrusion.

It is advantageous to arrange the gas cartridge with the opening device in the handle. This allows the entire device to be designed to be very short. Specifically gas cartridges filled with 16 g or 24 g of carbon dioxide are conceivable as gas cartridges. The use of others non-toxic gases, such as nitrogen, is feasible just as well.

The invention can just as well provide the compressed gas conduit to be formed by a hose connecting the opening device of the compressed gas cartridge to the opening of the hollow cylinder in gas-permeable manner, whereby a fabric-reinforced plastic hose is preferred as compressed gas conduit. Alternatively, plastic hoses jacketed with a metal mesh can be used just as well.

Figure 2:
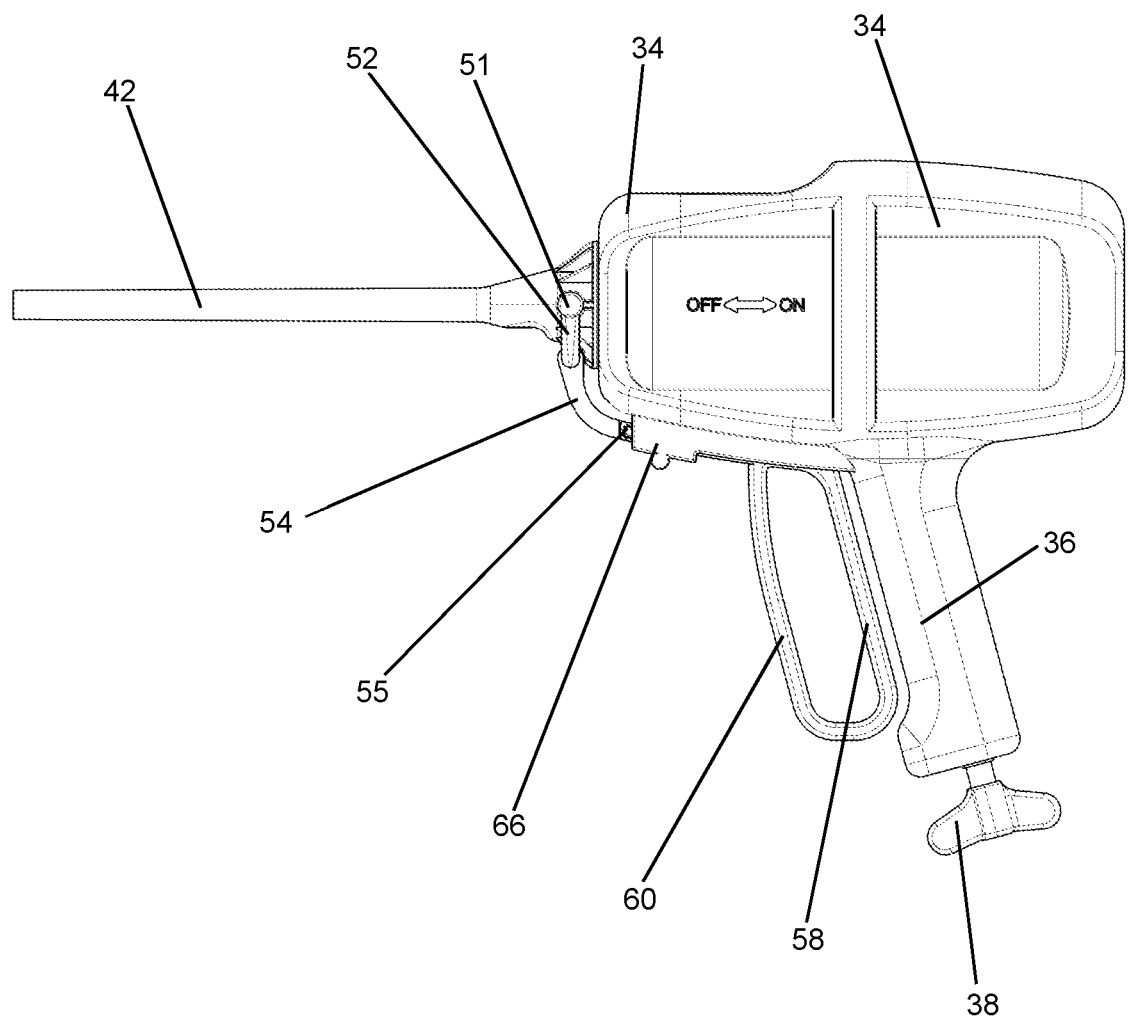
Figure 3:
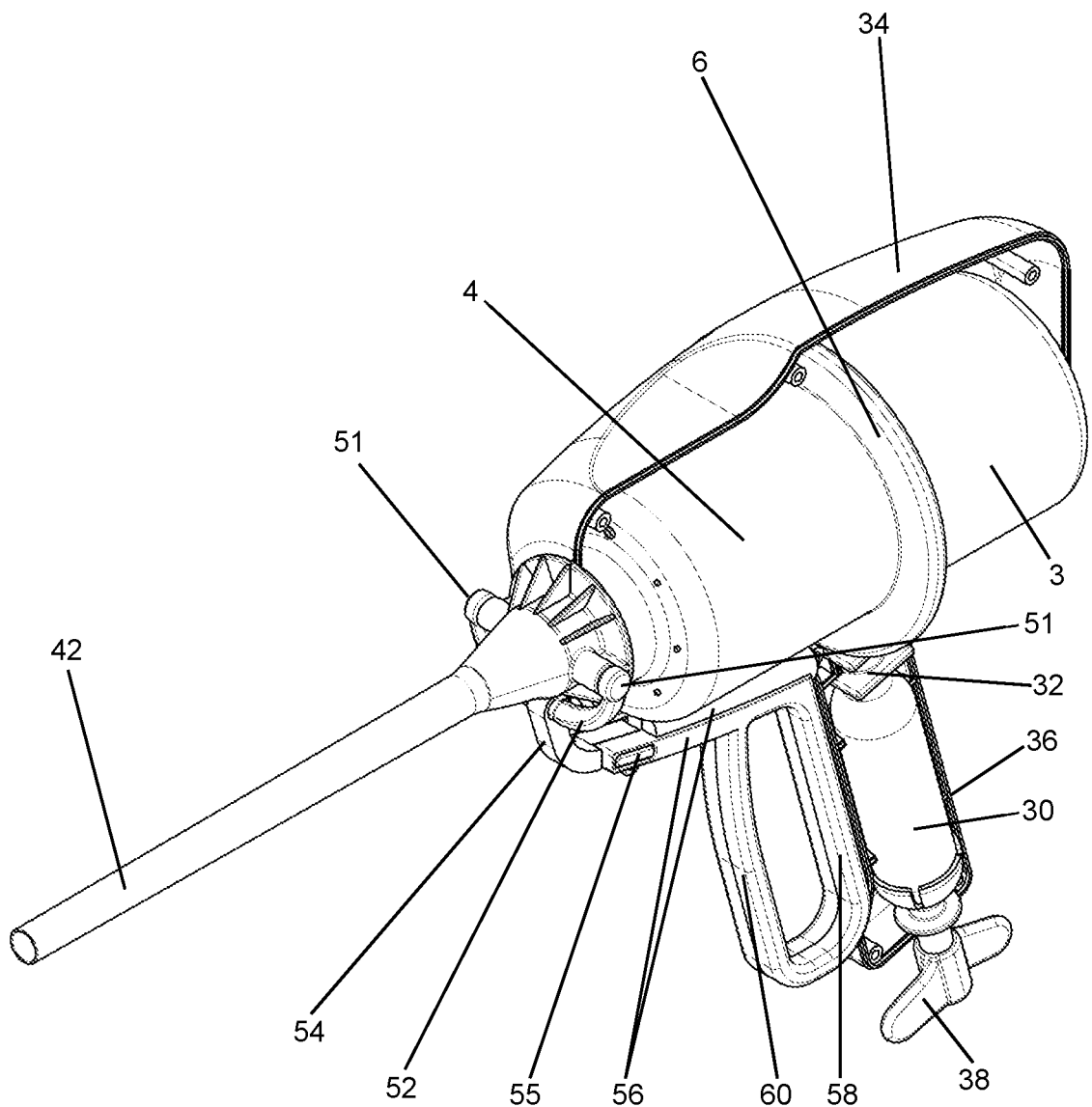
Figure 4:
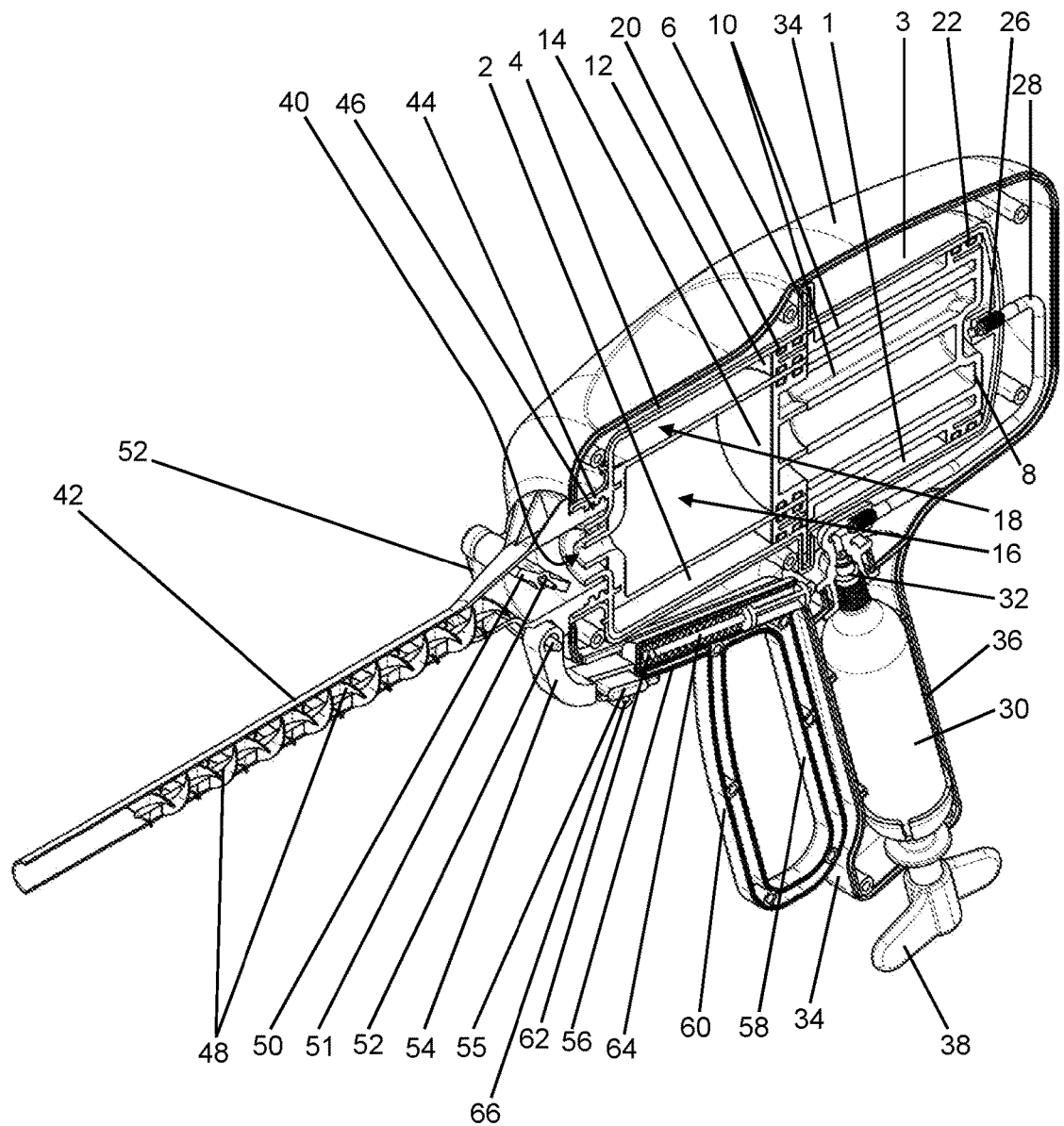
Figure 5:
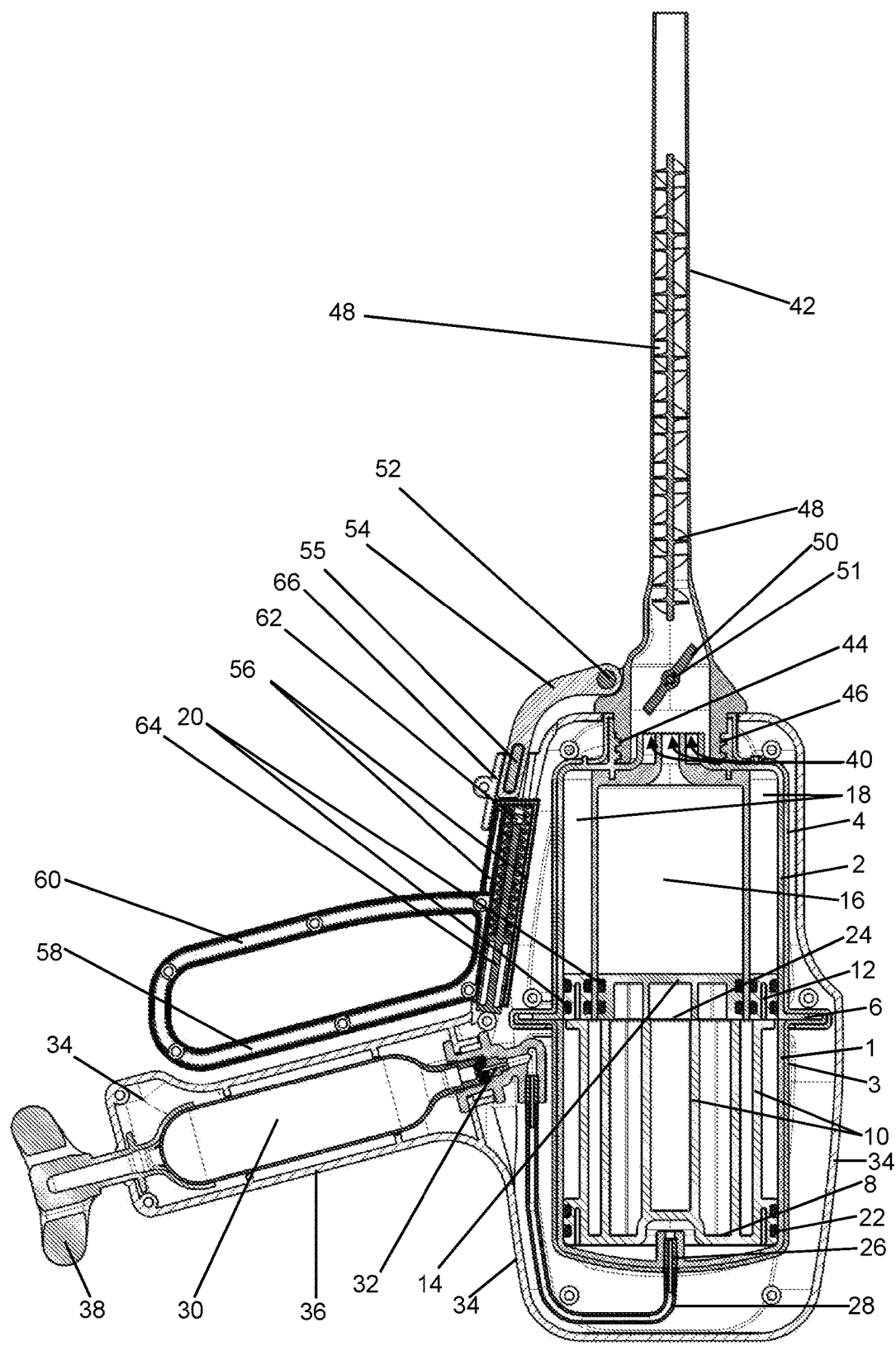
Figure 6:
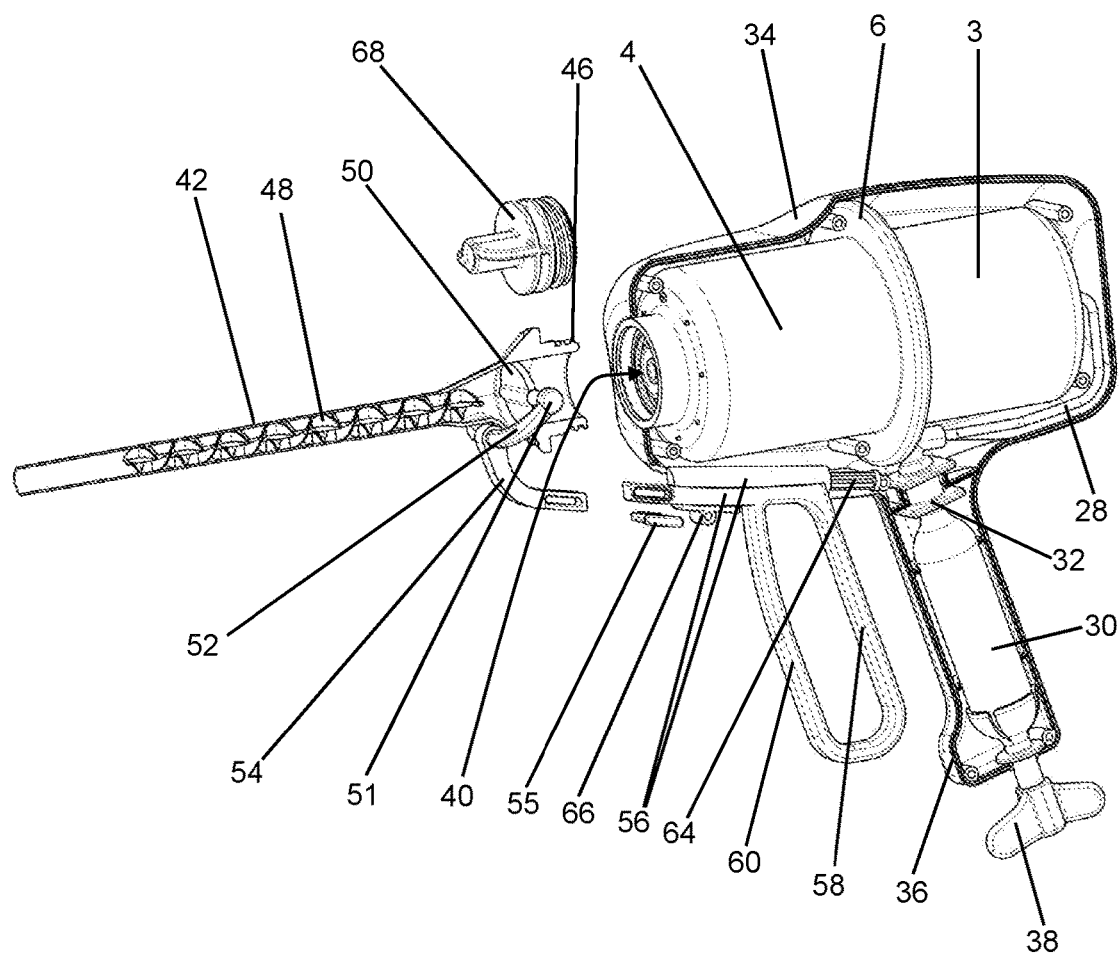
Figure 7:
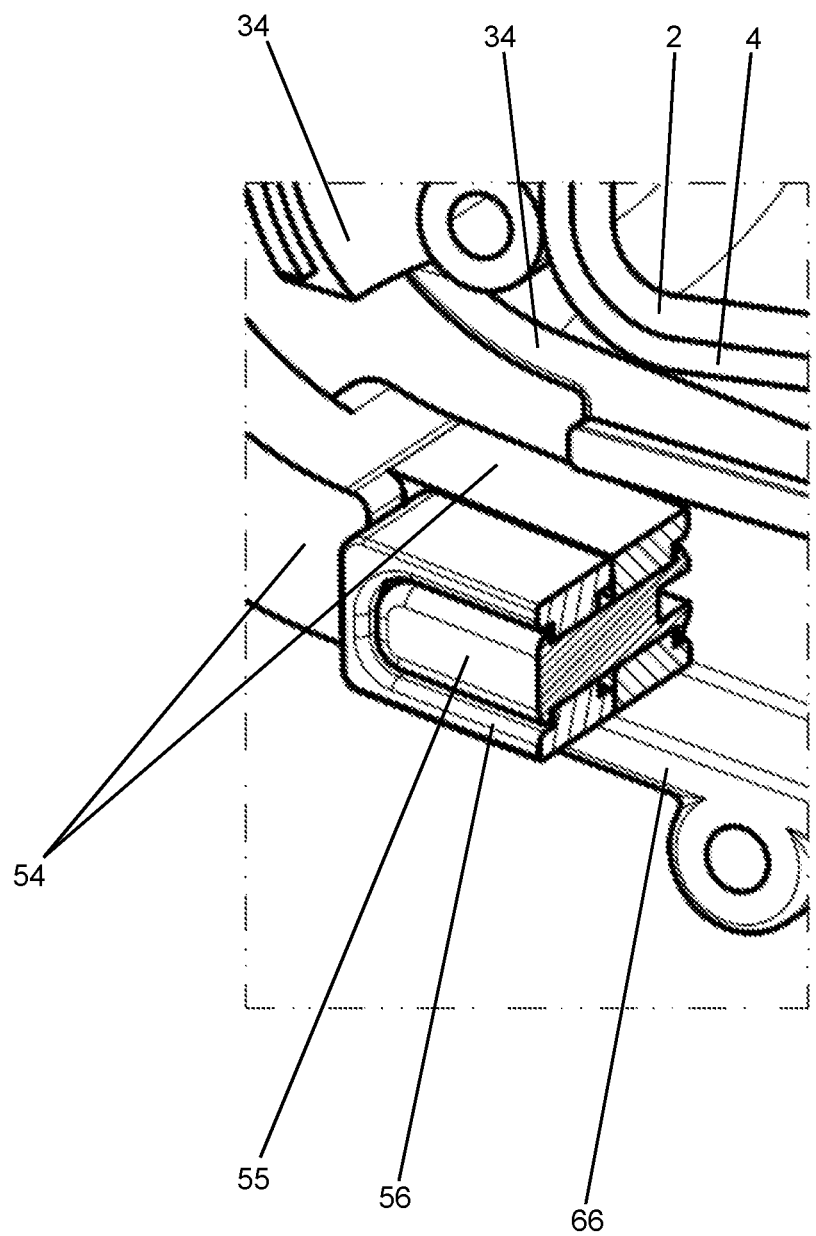

Further exemplary embodiments of the invention shall be illustrated in the following on the basis of seven schematic figures, though without limiting the scope of the invention. In the figures:

FIG. 1: shows a cross-sectional view of a paste application device according to the invention with the flap valve closed;

FIG. 2: shows a schematic side view of the paste application device according to FIG. 1 with the flap valve opened;

FIG. 3: shows a perspective view of the paste application device according to FIGS. 1 and 2 with the housing open and the flap valve opened;

FIG. 4: shows a schematic perspective cross-sectional view of the paste application device according to FIGS. 1 to 3 with the flap valve opened;

FIG. 5: shows a cross-sectional view of the paste application device according to FIG. 1 with the flap valve opened;

FIG. 6: shows a perspective view of the paste application device according to FIGS. 1 to 5 with open housing, separate dispensing tube and closure; and FIG. 7: shows an enlarged partial view of a connection of a rod assembly of the paste application device according to FIGS. 1 to 6.

FIGS. 1 to 7 show different views of a compressed gas-driven paste application device according to the invention and/or parts thereof. The paste application device is designed in the way of a pistol and can be held in one hand and can be operated with the same hand and/or the fingers of the same hand. A hollow cylinder 1 made of plastic material and a two-component cartridge 2, arranged adjacent to the former, are situated on the inside of the paste application device. The hollow cylinder 1 is surrounded by a first part 3 of a pressure vessel 3, 4 and the two-component cartridge 2 is surrounded by a second part 4 of the pressure vessel 3, 4. The two parts of the pressure vessel 3, 4 consist of a metallic material, such as an aluminium alloy, zinc or steel, and are connected to each other via a connection 6 in form-fitting manner by an outward-facing folded seam in material-bonded manner. The external walls of the hollow cylinder 1 and of the two-component cartridge 2 touch, by their surface, against the internal walls of the pressure vessel 3, 4 or are situated at a distance of maximally 100 µm to allow the pressure vessel 3, 4 to receive forces acting on the walls of the hollow cylinder 1 and two-component cartridge 2 without any deformation of the walls that would hamper the function of the paste application device. The hollow cylinder 1, the two-component cartridge 2, and the pressure vessel 3, 4 have a cylindrical shape and/or an essentially cylindrical shape.

A plunger 8 is provided as working plunger on the inside of the hollow cylinder 1 and can be used to convert the energy stored in the compressed gas into a linear motion along the cylinder axis and/or in longitudinal direction of the paste application device. Multiple pestles 10 that are arranged coaxially with respect to each other and are oriented in the direction of the two-component cartridge 2 are attached to the plunger 8. The pestles 10 can be used to drive two feed plungers 12, 14 that are arranged in the internal spaces 16, 18 of the two-component cartridge 2 that are arranged coaxially with respect to each other. The feed plungers 12, 14 are sealed with respect to the internal walls of the internal spaces 16, 18 by means of circumferential seals 20. Likewise, the plunger 8 touches in circumferential manner against the internal wall of the hollow cylinder 1 and is sealed in this place by means of circumferential seals 22.

Between the hollow cylinder 1 and the pestles 10 and the two-component cartridge 2, an aluminium composite foil 24 is taped onto the ends of the two-component cartridge 2 that are closed by the feed plungers 12, 14. The aluminium composite foil 24 is drawn in FIGS. 1 and 5 only and is omitted from FIG. 4 for reasons of clarity. The aluminium composite foil 24 seals the content of the two-component cartridge 2. Specifically if volatile ingredients are present in the starting components and are stored in the internal spaces 16, 18 of the two-component cartridge 2, these ingredients are prevented from escaping and thus the starting components are prevented from changing during storage. The aluminium composite foil 24 is simply punctured when the feed plungers are propelled with the pestles 10 of the plunger 8.

The compressed gas exits through a connector 26 and a compressed gas conduit 28 into the hollow cylinder 1, between the rear side of the plunger 8 and the closed side of the first part 3 of the pressure vessel 3, 4. For this purpose, the connector 26 projects through the single opening in the otherwise closed base surface of the first part 3 of the pressure vessel 3, 4 into the hollow cylinder 1. The hollow cylinder 1 and the first part of the pressure vessel 3, 4 are designed slightly curved on the back side (on the bottom in FIGS. 1 and 5, on the right in FIGS. 2 to 4). The connector 26 is seated, as a sleeve, in a sleeve of the hollow cylinder 1 and is designed for connection of the compressed gas conduit 28. The compressed gas conduit 28 consists of a fibre-reinforced plastic material.

A compressed gas cartridge 30 is connected to the compressed gas conduit 28 and can be opened by pushing the compressed gas cartridge 30 onto an opening means 32 in the form of a hollow mandrel 32 or puncturing mandrel 32. As a result, the compressed gas cartridge 30 opens and the compressed gas can flow through the compressed gas conduit 28 into the connector 26 and into the hollow cylinder 1, and can propel the plunger 8 in the direction of the two-component cartridge 2. The compressed gas cartridge 30 is preferred to be a liquid gas cartridge, in which, particularly preferably, carbon dioxide evaporates in order to provide the compressed gas.

The entire design specified thus far and/or all these parts (identified by reference numbers 1 to 32) are arranged inside a housing 34 made of plastic material. The housing 34 is provided, on the underside (on the left in FIGS. 1 and 5 and on the bottom in FIGS. 2, 3, 4, and 6), in the form of a handle 36 and/or pistol handle 36 by means of which the paste application device can be held. The compressed gas cartridge 30 has on its bottom side an operating device 38 attached to it that ends in a wing screw by means of which the compressed gas cartridge 30 can be screwed into a matching thread on the opening facility 32 and can be opened by means of the hollow mandrel 32 or puncturing mandrel 32. Accordingly, the paste application device can be activated manually and/or made ready for use by operating the operating device 38 and thus opening the compressed gas cartridge 30.

The front side of the cylindrical part of the two-component cartridge 2 and the coaxially arranged internal spaces 16, 18 situated inside converge conically and merge in dispensing openings 40 through which the starting components can be expelled from the internal spaces 16, 18 from the two-component cartridge 2. The starting components are mixed with each other downstream from the dispensing openings 40. In the storage state of the paste application device, the dispensing openings 40 are initially closed by a screw closure 68 (shown in FIG. 6 only). In the application state, the closure 68 is removed and a dispensing tube 42 is attached on the front face in its stead. For this purpose, an internal thread 44 is provided on the front face, in a socket on the two-component cartridge 2. An external thread 46 of the dispensing tube 42 is screwed into said internal thread 44. The closure 68 comprises an analogous external thread that was and/or can be screwed into the internal thread 44 of the two-component cartridge 2 in order to close the dispensing openings 40.

A static mixer 48 is provided on the inside of the dispensing tube 42 and can be used to mix the starting components when these flow through the dispensing tube 42. The flow through the dispensing tube 42 can be controlled by means of a manually operable flap valve 50 that is supported in the channel of the dispensing tube 42 such that it can rotate about a rotary axis 51. When the flap valve 50 is closed, the starting components can no longer be expelled from the two-component cartridge 2 and, accordingly, the feed plungers 12, 14 and the plunger 8 cannot be propelled any further. By not simply interrupting the gas flow, in contrast to other application devices known from the prior art, the gas already introduced cannot expand further and the paste mixture cannot continue to flow in undesired manner. Arranging the flap valve 50 in the channel of the dispensing tube 42 is expedient, since the load on the bearings of the flap valve 50 is limited due to the small cross-section.

Multiple ventilation openings (not shown) are provided one above the other in the hollow cylinder 1 and the first part of the pressure vessel 3. The ventilation openings can be arranged, for example, at a level of the hollow cylinder 1 that corresponds at least, and preferably, to approximately the level of the plunger 8 such that, upon the plunger 8 being propelled in the direction of the two-component cartridge 2 to the limit stop, the region between the plunger 8 and the rear side of the hollow cylinder 1 is opened with respect to the surroundings by means of the ventilation openings and the remaining pressure can escape into the surroundings. This ensures that the spent paste application device is no longer pressurised during recycling or disposal and can therefore be processed and/or disassembled without any hazard.

The flap valve 50 can be operated from outside the paste application device in that an arch 52 is connected to the two ends of the rotary axis 51 of the flap valve 50 such that the arch 52 encompasses the flap valve 50. A rod 54 and/or a rod assembly 54 is connected to the arch 52 at the apex of the arch 52 such as to be rotatable. The apex of the arch 52 forms the axis about which the rod assembly 54 is supported such as to be rotatable with respect to the arch 52. The rod assembly 54 extends in the direction of the handle 36 and is mobile in said main direction, namely the longitudinal direction of the rod assembly 54. The flap valve 50 can be opened and closed by this motion via the arch 52. The rod assembly 54 is connected to a rear part of the rod assembly 56 via a connecting element 55 in the form of a slider 55 having a snap-in element (see FIG. 7). The purpose of the snap-in element is to make sure that the slider 55 cannot inadvertently become detached from the eyelets of the rod assembly 54, 56, which would lead to detachment of the rod assembly 54, 56

Said two-part design of the rod assembly 54, 56 allows the flap valve 50 to be attached to the dispensing tube 42 as part thereof only briefly before the use of the paste application device. As a result, the closure 68, which is much better suited for storage of the starting components in the internal spaces 16, 18 than the closed flap valve 50, can stay attached to the two-component cartridge 2 for as long as possible. In the absence of the closure 68, the starting components can react with each other and become cured in the region in front of the dispensing openings 40 such that the paste application device would then no longer be usable.

The rod assembly 54, 56 can be operated by means of a trigger 58, 60. The trigger 58, 60 comprises two bars or levers 58, 60 that are situated at a distance from each other and can be operated by the fingers of the hand that holds the paste application device on handle 36. A steel spring 62 is supported, as restoring element 62, via a rod 64 on the housing 34, in the region of the base of the handle 36, and acts appropriately on the rod assembly 54, 56 such that the rod assembly 54, 56 is being pushed away from the handle 36. By this means, the flap valve 50 is pushed into the closed position by the steel spring 62. The flap valve 50 is opened and the steel spring 62 is tensioned by pulling the trigger 58, 60 on the first part 58 in the direction of the handle 36 (see FIGS. 2, 3, 4, 5).

The rod assembly 56 is supported in a guidance 66 that is attached to the housing 34 and thus is rigidly connected to the hollow cylinder 1. The guidance 66 defines the main direction of the motion of the rod assembly 54, 56. Due to the rotary motion of the arch 52 and the linear motion of the rod assembly 54, 56, there is a need to have some clearance in the bearing in a direction perpendicular to the main direction (to the left and right in FIGS. 1 and 5; upward and downward in FIGS. 2 to 4 and 6 and 7). In the absence of this clearance, the rod assembly 54, 56 would either be bent too strongly or become lodged in the guidance 66. Depending on the size of the design of the paste application device, the clearance should be at least 0.3 mm or up to at least 2 mm.

The tensioned steel spring 62 pushes the rod assembly 54, 56 forward and opens the flap valve 50, when no force acts any longer on the first part 58 of the trigger 58, 60 in the direction of the handle 36. An additional force may be applied to overcome the adhesive friction and to ultimately close the flap valve 50 by the back sides of the fingers of the hand that also holds the handle 36 exerting a pressure onto the second part 60 of the trigger 58, 60 in the direction away from the handle 36. The trigger 58, 60 is designed appropriately such that multiple fingers of the hand reach through the opening of the trigger 58, 60 in order to operate the trigger 58, 60.

An internal thread is provided in the region of the opening means 32 and can have an external thread of the compressed gas cartridge 30 screwed into it. A gasket is provided between the connector and the compressed gas cartridge 30 and/or between the hollow mandrel 32 and the compressed gas cartridge 30 in order to enable a pressure-tight connection to the compressed gas conduit 28.

The rotary axis 51 of the flap valve 50 is a steel axle 51 about which the flap valve 50 can be rotated in the dispensing tube 42 by means of the arch 52. The steel axle 51 provides the needed stability of the flap valve 50. The steel axle 51 must not be subject to plastic deformation under the effect of the pressure from the compressed gas cartridge 30, mediated by the starting components, to the extent that the function of the flap valve 50, for example the mobility of the flap valve 50, would no longer be ensured. Rotating the flap valve 50 about the steel axle 51 allows the volume flow through the dispensing tube 42 to be controlled, while the gas pressure mediated by the plunger 8 and the feed plungers 12, 14 expels the content from the two-component cartridge 2, i.e. expels the starting components from the two-component cartridge 2.

The features of the invention disclosed in the preceding description and in the claims, figures, and exemplary embodiments, can be essential for the implementation of the various embodiments of the invention both alone and in any combination.

LIST OF REFERENCE NUMBERS

1 Hollow cylinder
2 Two-component cartridge
3 Pressure vessel, first part
4 Pressure vessel, second part
6 Connection
8 Plunger
10 Pestle
12 Feed plunger
14 Feed plunger
16 Inner internal space
18 Outer internal space
20 Gasket
22 Gasket
24 Aluminium composite foil
26 Compressed gas connector
28 Compressed gas conduit
30 Compressed gas cartridge
32 Opening means with puncturing mandrel/hollow mandrel
34 Housing
36 Handle
38 Operating facility
40 Dispensing opening
42 Dispensing tube
44 Internal thread
46 External thread
48 Static mixer
50 Rotatable flap valve
51 Rotary axis of the flap valve
52 Arch/yoke
54 Rod assembly
55 Connecting element/slider
56 Rod assembly/rod
58 Trigger/first part of the trigger
60 Trigger/second part of the trigger
62 Spring/restoring element
64 Rod
66 Guidance
68 Closure

The invention claimed is:

1. A paste application device for storage of two starting components, for mixing the starting components to form a paste, and for application of the formed paste, the device comprising
   a two-component cartridge comprising two internal spaces, two feed plungers that are shiftable in the internal spaces and border the internal spaces on a first side of the two-component cartridge, and at least two dispensing openings by means of which the internal spaces are open on a second side of the two-component cartridge that is opposite from the first side, and
   a hollow cylinder that is made of a plastic material and has one front face that is open and one front face that is partially closed, in which is situated an axially mobile plunger that has two pestles attached thereto, wherein the at least two pestles are oriented in the direction of the open front face, wherein the open front face of the hollow cylinder is arranged to axially touch against the first side of the two-component cartridge, and wherein the plunger closes in gas-tight manner against the internal walls of the hollow cylinder,
   wherein the two-component cartridge and the hollow cylinder are arranged in a pressure vessel,
   wherein the hollow cylinder comprises, on the front face that is partially closed, a connector for a compressed gas cartridge that extends through an opening in the pressure vessel,
   wherein a manually operable flap valve is arranged downstream from the dispensing openings or a dispensing tube having a manually operable flap valve is attachable downstream from the dispensing openings, wherein the flap valve thus arranged is usable to regulate the volume flow of the starting components through the dispensing openings, and
   wherein the flap valve is operable by means of a rod assembly of the paste application device, wherein the rod assembly is supported such as to be mobile in one main direction with respect to the hollow cylinder and is supported with a clearance of at least 0.3 mm in at least one direction that is perpendicular to the main direction.

2. The Paste application device according to claim 1, wherein at least one restoring element acts on the rod assembly and/or the flap valve such that the restoring element rotates the flap valve into the closed position, wherein the at least one restoring element can be tensioned by pulling the trigger.

3. The paste application device according to claim 1, wherein the rod assembly has a two-part design, wherein the two parts of the rod assembly are connectable to each other by means of a bolt, slider or a snap-in element and are connectable to each other in a form-fitting manner, wherein a first part of the rod assembly is connected to the dispensing tube and a second part of the rod assembly is connected to the hollow cylinder.

4. The paste application device according to claim 1, further comprises a manually operable trigger by means of which the rod assembly is movable in the main direction and by means of which the flap valve can thus be operated.

5. The paste application device according to claim 4, wherein the trigger comprises two levers situated at a distance from each other between which at least one finger of a hand can reach such that the trigger is movable in both directions with the at least one finger of the hand, wherein the first lever is operated by pulling the trigger and thus opens the flap valve, and the second lever is operated by pushing the trigger in reverse direction and thus closes the flap valve.

6. The paste application device according to claim 4, wherein the trigger transitions the flap valve from the closed to the maximally opened state by means of a stroke of maximally 100 mm.

7. The paste application device according to claim 6, wherein the restoring element is a compression spring that is supported on a part of a housing that is connected to the hollow cylinder.

8. The paste application device according to claim 1, wherein the pressure vessel touches against the hollow cylinder or is situated at a distance of at most 0.4 mm from the hollow cylinder.

9. The paste application device according to claim 1, wherein a compressed gas conduit is connected to the connector for the compressed gas cartridge, wherein the compressed gas conduit connects the connector to the compressed gas cartridge or to an opening device for the compressed gas cartridge, wherein the compressed gas conduit is a fabric-reinforced plastic hose.

10. The paste application device according to claim 1, wherein the pressure vessel is made from metal, a metallic alloy, a high-strength plastic material, a fibre-reinforced plastic material or a combination thereof.

11. The paste application device according to claim 1, further comprising a yoke or an arch attached on the rotary axis of the flap valve in force-locking or form-fitting manner and the yoke or arch is connected to the rod assembly by means of an axle.

12. The paste application device according to claim 11, wherein the axle, by means of which the yoke or the arch is connected to the rod assembly, is arranged such as to be parallel to the rotary axis of the flap valve, wherein the axle is arrangeable on an apex of the arch or yoke.

13. The paste application device according to claim 1, further comprising a handle arranged on the paste application device by means of which the paste application device can be held with one hand, wherein the rod assembly is operable with the same hand by means of the trigger, and thus the flap valve is openable or closable with the same hand.

14. The paste application device according to claim 13, wherein the trigger, with the flap valve in its closed state, is situated at a distance of maximally 30 mm from the handle and the trigger, with the flap valve in its maximally opened state, touches against the handle or is situated at a distance of no more than 10 mm from the handle.

15. The paste application device according to claim 13, wherein the compressed gas cartridge or the compressed gas cartridge and an opening device for opening the compressed gas cartridge is/are arranged in the handle.

16. The paste application device according to claim 1, wherein the flap valve is arranged in a conduit that is formed by a dispensing tube, wherein a static mixer in the dispensing tube is provided by means of which the starting components are mixable while flowing through the static mixer.

17. The paste application device according to claim 1, wherein the pressure vessel has a two-part design, wherein the two parts are connected to each other in force-locking manner by riveting, by a screw connection and/or by a union nut, wherein a first part of the two parts of the pressure vessel contains the two-component cartridge and the second part of the two parts of the pressure vessel contains the hollow cylinder.

18. The paste application device according to claim 1, wherein the two-component cartridge, or at least regions thereof, is a coaxial cartridge, wherein one of the internal spaces in the coaxial cartridge is cylindrical and situated inside and the other internal space is cylindrical and coaxially surrounds the inner internal space.

19. The paste application device according to claim 1, further comprising a closure for closing the dispensing openings that can be fastened by means of a thread of the closure, to an opposite thread in the region of the dispensing openings, wherein the dispensing tube, comprising a corresponding fastening means, is fastenable to the opposite fastening means.

20. The paste application device according to claim 1, further comprising a protective foil/film arranged between the hollow cylinder and the two-component cartridge and the protective foil/film closes the internal spaces of the two-component cartridge on the first side, wherein the protective foil/film is pasted, welded or bonded onto the two-component cartridge.

21. The paste application device according to claim 1, wherein at least one through-going ventilation opening is provided in the external wall of the hollow cylinder, half facing in the direction of the two-component cartridge, and in the wall of the pressure vessel such that the pressure escapes from the hollow cylinder, when the plunger is arranged between the ventilation opening and the two-component cartridge.

22. The paste application device according to claim 1, wherein the two-component cartridge, the hollow cylinder, and the pressure vessel are arranged in a housing, wherein the pressure gas cartridge is arranged in the housing and/or the housing is provided as a handle on an underside of the paste application device.

23. A method for mixing and dispensing a paste, the method comprising:

conducting a compressed gas from a compressed gas cartridge through a connector of a hollow cylinder into the hollow cylinder, wherein a pressure vessel receives a force of the compressed gas acting on the walls of the hollow cylinder and a plunger with pestles is propelled by the compressed gas in the hollow cylinder in the direction of the two-component cartridge;

driving, with the propelled pestles of the plunger, drive feed plungers forward into at least two internal spaces of the two-component cartridge, wherein the starting components are expellable from the internal spaces of the two-component cartridge through the at least two dispensing openings of the internal spaces;

stopping flow of the starting components by a closed flap valve downstream from the dispensing openings, and a yoke or an arch is rotated by a manual operation of an operating element such that the rotary axis of the flap valve connected to the yoke or arch is rotated such that the flap valve is opened and the starting components and/or the mixture thereof flow(s) through the opened flap valve, and the mixture is applicable after mixing the starting components; and moving a rod assembly by the manual operation of the operating element, wherein the yoke or the arch is rotatable by the motion such that the rotary axis of the flap valve that is connected to the yoke or arch is rotatable such that the flap valve is openable.

24. The method according to claim 23, wherein the paste application device according to claim 1 is utilized to implement the method.

25. The method according to claim 23, further comprising:

closing the flap valve through action of a force of an elastic spring, and/or through a manual operation of the operating element in the direction reverse to the operation for opening the flap valve.

* * * * *